United States Patent
Hossick-Schott et al.

(10) Patent No.: US 7,342,774 B2
(45) Date of Patent: Mar. 11, 2008

(54) ADVANCED VALVE METAL ANODES WITH COMPLEX INTERIOR AND SURFACE FEATURES AND METHODS FOR PROCESSING SAME

(75) Inventors: Joachim Hossick-Schott, Minneapolis, MN (US); John D. Norton, New Brighton, MN (US); Anthony W. Rorvick, Champlin, MN (US); Steve J. May, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 334 days.

(21) Appl. No.: 10/692,649

(22) Filed: Oct. 23, 2003

(65) Prior Publication Data

US 2004/0134874 A1 Jul. 15, 2004

Related U.S. Application Data

(60) Provisional application No. 60/429,304, filed on Nov. 25, 2002.

(51) Int. Cl.
*H01G 9/04* (2006.01)

(52) U.S. Cl. ............... 361/528; 361/508; 361/509; 361/523; 361/525; 361/516

(58) Field of Classification Search ........ 361/523–525, 361/528–532, 502–504, 508–512; 29/25.03
See application file for complete search history.

(56) References Cited

U.S. PATENT DOCUMENTS

| | | | |
|---|---|---|---|
| 3,345,545 A | 10/1967 | Bourgault et al. | |
| 4,184,192 A * | 1/1980 | Yoshida et al. | 361/532 |
| 4,599,788 A | 7/1986 | Love et al. | |
| 5,189,770 A | 3/1993 | Waidhas et al. | |
| 5,369,547 A | 11/1994 | Evans | |
| 5,469,325 A | 11/1995 | Evans | |
| 5,522,851 A | 6/1996 | Fayram | |
| 5,559,667 A | 9/1996 | Evans | |
| 5,584,890 A | 12/1996 | MacFarlane et al. | |
| 5,801,917 A | 9/1998 | Elias | |

(Continued)

FOREIGN PATENT DOCUMENTS

GB 1 540 332 12/1977

OTHER PUBLICATIONS

Power Geometry and Structural Design of the High Volumetric Efficiency Tantalum Electrolytic Capacitor—IEEE Transactions on Parts, Hybrids, and Packaging, vol. PHP-9, No. 3, September 1793—Stephen E. Hluchan.
Approaching the Limits: The Latest Developments in Solid Tantalum Capacitors—Electronic Engineering Oct. 1991—Bill Millman.
Carts '98 Program—Lowest ESR Tantalum Chip Capacitor, Eric K. Reed, Jim C. Marshall, John D. Prymak.

(Continued)

*Primary Examiner*—Nguyen T. Ha
(74) *Attorney, Agent, or Firm*—Paul H. McDowall; Steve Bauer

(57) ABSTRACT

The present invention generally relates to improved capacitors; in particular, the present invention provides advanced valve metal (AVM) anodes and methods for fabricating AVM anodes having complex surface and interior features for use in high energy density capacitors. Such anodes find use in high voltage capacitors incorporated into implantable medical devices (IMDs), among other uses. The AVM anodes may be pressed into virtually any arbitrary shape and may have a gradually changing (or substantially constant) density profile throughout the AVM anode. Such AVM anodes may also be perforated or shaped to receive one or more cathode members. The AVM anodes enhance packaging efficiency for compact high energy density capacitors.

19 Claims, 4 Drawing Sheets

U.S. PATENT DOCUMENTS

| | | |
|---|---|---|
| 5,837,121 A | 11/1998 | Kinard et al. |
| 5,908,151 A | 6/1999 | Elias et al. |
| 5,983,472 A | 11/1999 | Fayram et al. |
| 6,006,133 A | 12/1999 | Lessar et al. |
| 6,231,993 B1 | 5/2001 | Stephenson et al. |
| 6,235,181 B1 | 5/2001 | Kinard et al. |
| 6,238,810 B1 | 5/2001 | Strange et al. |
| 6,275,729 B1 | 8/2001 | O'Phelan et al. |
| 6,375,688 B1 * | 4/2002 | Akami et al. ............... 29/25.03 |
| 6,409,776 B1 | 6/2002 | Yan et al. |
| 6,413,409 B1 * | 7/2002 | Otowa et al. ............... 205/748 |
| 6,519,137 B1 * | 2/2003 | Nitta et al. ................. 361/525 |
| 6,576,524 B1 * | 6/2003 | Evans et al. ................. 438/381 |
| 6,709,946 B2 * | 3/2004 | O'Phelan et al. ........... 438/396 |
| 6,801,424 B1 * | 10/2004 | Nielsen et al. .............. 361/517 |

OTHER PUBLICATIONS

Carts—Europe '98—Lowest ESR Tantalum Chip Capacitor, Eric K. Reed, Jim C. Marshall, John D. Prymak.

Carts '99-18 Milliohms and Falling—New Ultra-Low ESR Tantalum Chip Capacitors, Eric K. Reed, Jim C. Marshall.

Carts—Europe '99—Lowest Available ESR Conformally-Coated Multiple-Anode Tantalum Capacitor—Jeremy Ladd, Vishay Sprague.

Carts—Europe 2001—Improved ESR on $MnO_2$ Tantalum Capacitors at Wide Voltage Range—I. Horacek, T. Zednicek, M. Komarek, J. Tomaso, S. Zednicek, W. A. Millman, J. Sikula, J. Hlavka.

Carts 2002—Lowest ESR Tantalum Capacitors With High CV Values—H. Zillgen, V. Döge, W. Braunwarth.

* cited by examiner

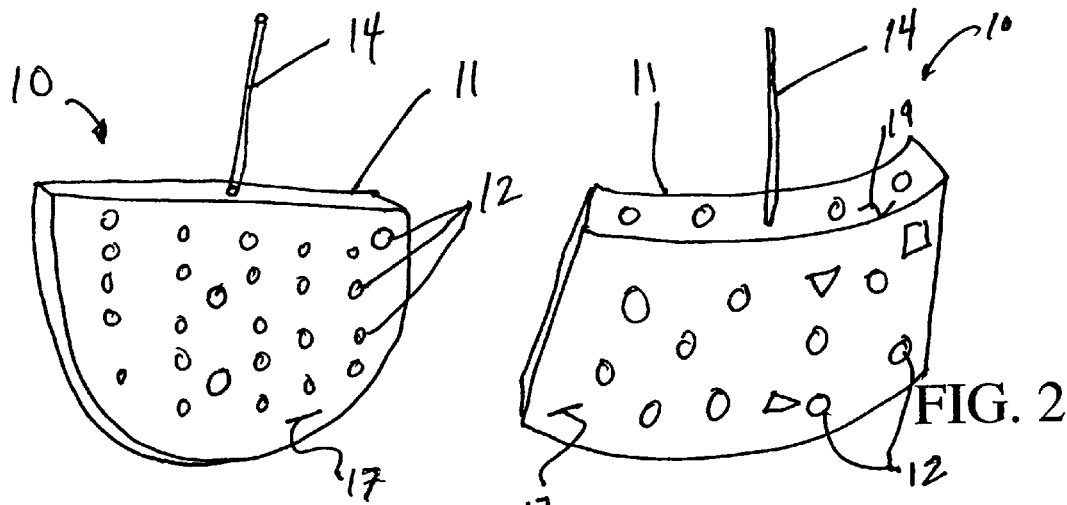
FIG. 1
FIG. 2
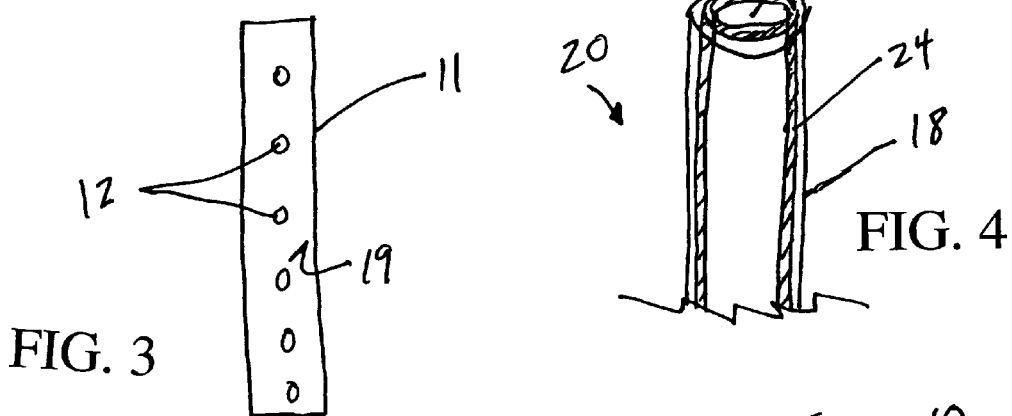
FIG. 3
FIG. 4
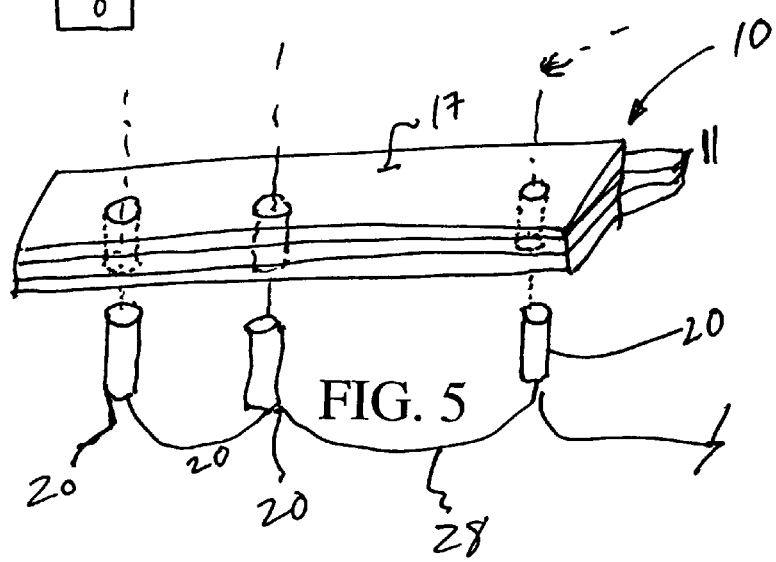
FIG. 5

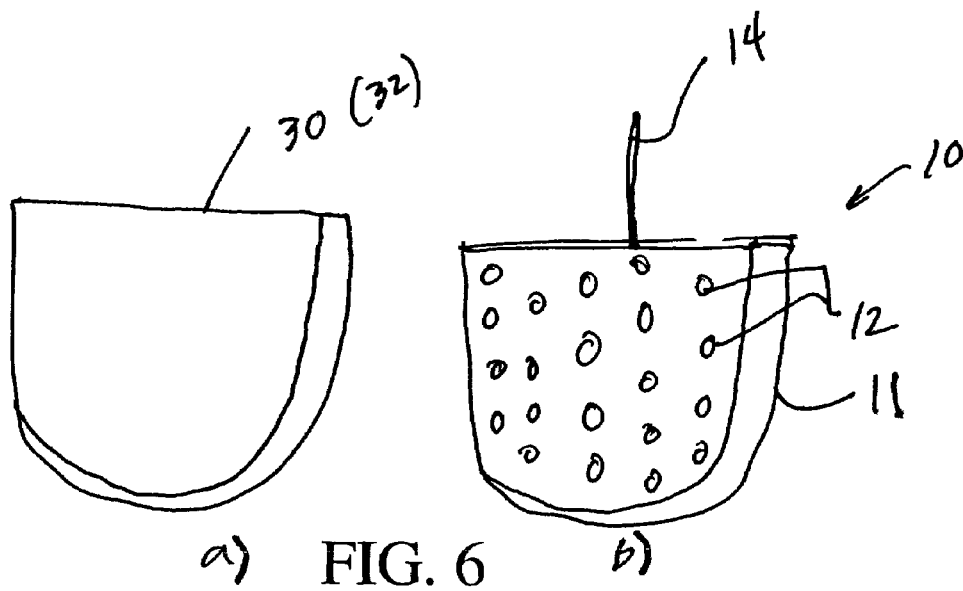
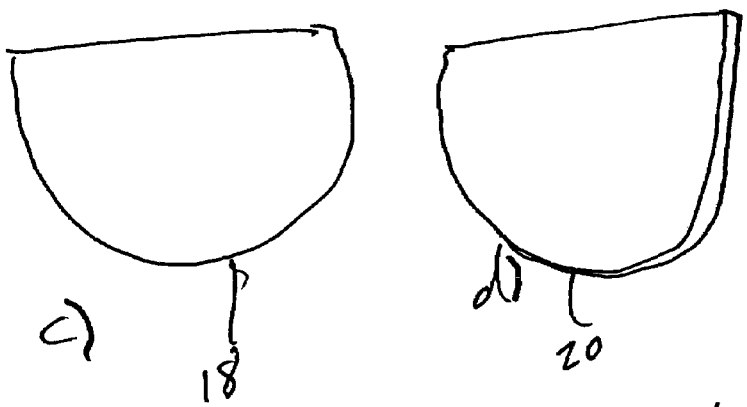
FIG. 6
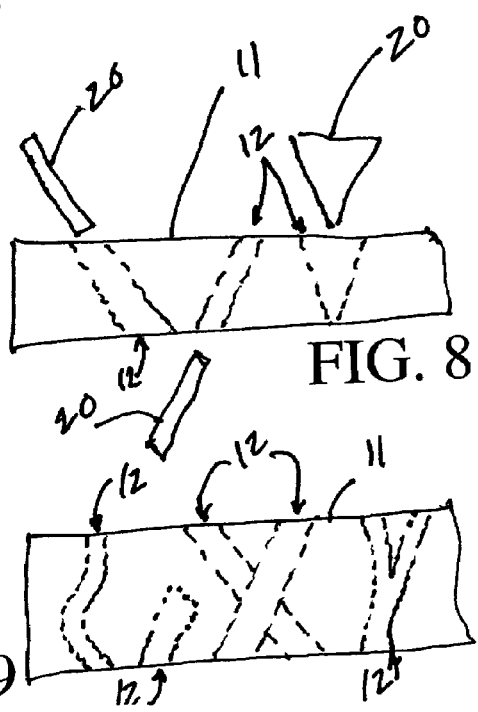
FIG. 7
FIG. 8
FIG. 9

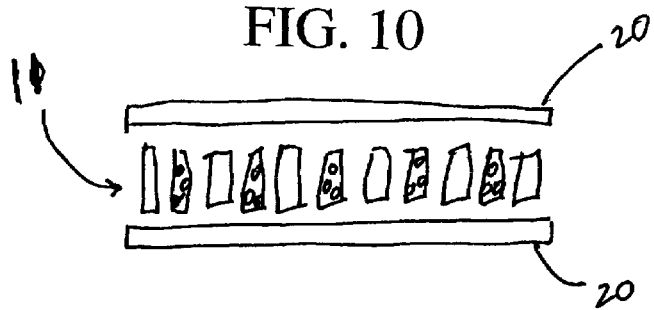
FIG. 10
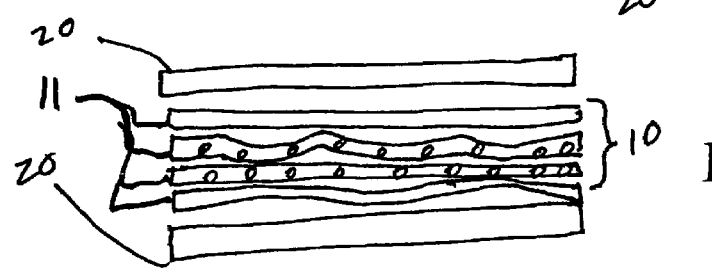
FIG. 11
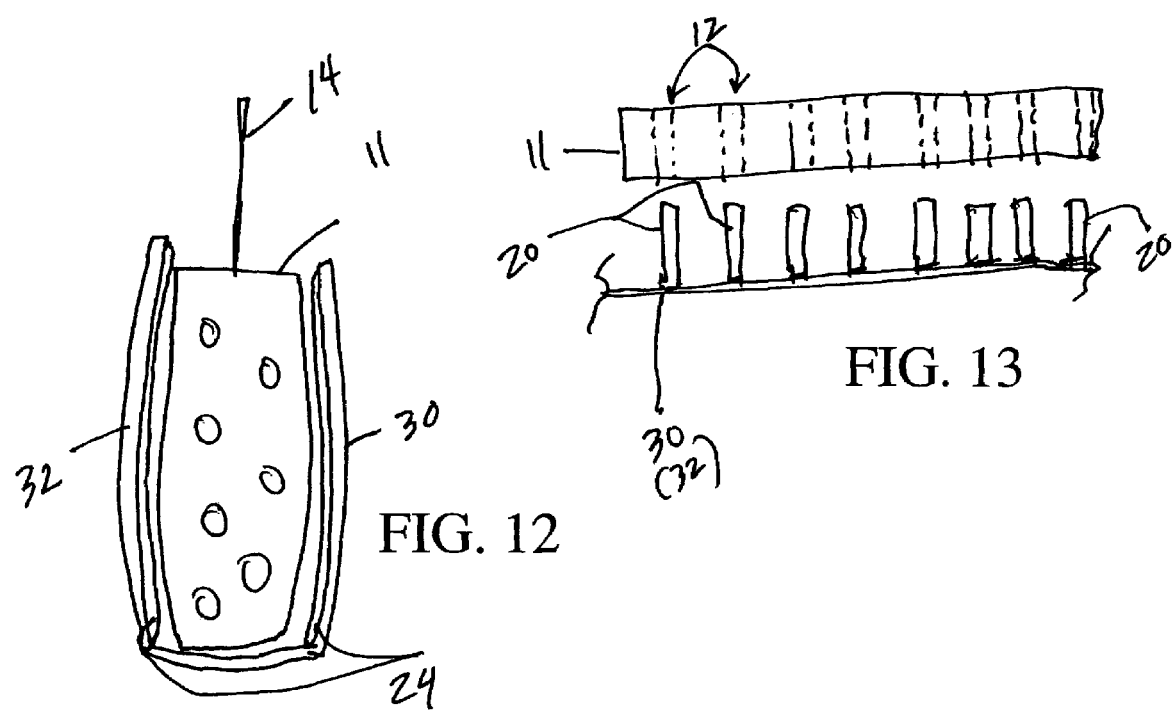
FIG. 12
FIG. 13

ADVANCED VALVE METAL ANODES WITH COMPLEX INTERIOR AND SURFACE FEATURES AND METHODS FOR PROCESSING SAME

CROSS REFERENCE TO RELATED APPLICATION

The present non-provisional patent application claims the benefit of provisional patent application Ser. No. 60/429,304 filed 25 Nov. 2002 and entitled, "ELECTROLYTIC VALVE METAL ANODES INCORPORATING A TUNNEL OR CHANNEL ARRAY," the contents of which are hereby incorporated by reference herein.

FIELD OF THE INVENTION

The present invention generally relates to improved capacitors; in particular, the present invention provides advanced valve metal (AVM) anodes and methods for fabricating AVM anodes having complex surface and interior features for use in high energy density capacitors. More particularly, such anodes find use in high voltage capacitors incorporated into implantable medical devices (IMDs), among other uses.

BACKGROUND OF THE INVENTION

The term "valve metal" represents a group of metals including aluminum, tantalum, niobium, titanium, zirconium, etc., all of which form adherent, electrically insulating metal-oxide films upon anodic polarization in electrically conductive solutions. The performance of valve metal and other types of capacitors depends upon several factors (e.g., the effective surface area of the anodes and cathodes that can be contacted by electrolyte, the dielectric constant of the oxide formed on the metal surface, the thickness of the oxide layer on top of the metal surface, the conductivity of the electrolyte, etc.). The thickness of the anodic oxide layer is approximately proportional to the electrical potential applied to the anode during the formation of the anode (i.e., at the time when the anode is immersed into the formation electrolyte). For aluminum, the oxide grows approximately by ~1.0 nm per Volt, for tantalum this "growth rate" is somewhat higher, approximately 1.7 nm per Volt. Niobium and tantalum anodes are typically made in the form of a pressed powder pellet or "slug" when used in an electrolytic capacitor.

The density of the pressed anode slug is typically significantly less than the density of the bulk metal of which the powder is made, i.e., up to ⅔ of the volume of a given slug may be open space (pore space). The final density of the anode slug is largely determined at the time of pressing, when a known amount of powder is pressed into a known volume. Traditionally, formation of the anode slug has been thought to require a fairly homogeneous distribution of open space throughout the anode slug since the forming electrolyte needs to wet even the most "remote" cavities in the karst-like internal structure of the anode. This is specifically important for comparatively large anodes with volumes of the order 1 cm³ or above.

Furthermore, free flow of liquid electrolyte, both during initial surface processing (e.g., formation of surface oxide on the anode, also referred to as anodization) and operation as an electrochemical cell, continues to dominate capacitor design. One reason relates to the fact that the electrolyte used during anodization, typically referred to as a "formation electrolyte," can become overheated within the interstices of the anode. This overheating adversely affects oxide formation and may cause electrolyte residue to accumulate, further compromising performance of the completed electrochemical cell. During operation of the electrochemical cell continued free circulation of the electrolyte, typically referred to as the "working electrolyte," is required for rapid charge transfer. Such charge transfer occurs during charge and discharge cycling of the capacitor.

During formation, a power source capable of delivering a constant electrical current of about 100 mA per anode and a constant electrical potential of several hundred volts is connected to the anode slug that is immersed in the electrolyte. Electrical energy as high as 10 Watts per anode may be dissipated as heat and local differences in applied electrical potential may be encountered.

Regardless of the process by which the valve metal powder was processed, pressed and sintered valve metal powder structures, and specifically tantalum and niobium pellets, are typically anodized by the controlled application of formation potential and electrical current while the anode is immersed in the formation electrolyte. A typical formation electrolyte consists of ethylene glycol or polyethylene glycol, de-ionized water and $H_3PO_4$ and has a conductivity anywhere between 50 µS/cm (read: micro-Siemens per cm) to about 20,000 µS/cm at 40° C. Conventional practice has been to form the anodically polarized valve metal to a target formation potential with a constant electrical current flowing through the anode-electrolyte system. Typically, stainless steel cathodes are used with the glycol-containing electrolytes.

In the context of medical devices, capacitors are typically charged and discharged rapidly for delivery of low voltage or high voltage stimuli. Upon or during detection of a potentially lethal arrhythmia, suitable electrical transformer circuitry charges one or more high voltage capacitors using a low voltage battery as a charge source. Then, at an appropriate time the energy stored in the capacitor(s) discharges through a pair of electrodes disposed in or near a patient's heart. The magnitude of the discharged energy is used to terminate the arrhythmia and commence organized cardiac activity. Medical devices that deliver cardioversion and/or defibrillation therapy include automated external defibrillators (AEDs) and implantable cardioverter-defibrillators (ICDs). For purposes of the present invention, an ICD is understood to encompass all such IMDs having at least high voltage cardioversion or defibrillation capabilities. In most all IMDs, energy, volume, thickness and mass are critical features. The battery(s) and high voltage capacitor(s) used to provide and accumulate the energy required for the effective cardioversion/defibrillation therapy have historically been relatively bulky and expensive.

SUMMARY

The present invention provides improved capacitor fabrication techniques and devices wherein pre-processing of valve metal anodes provides diverse complex anode shapes and promotes free circulation of liquid electrolyte in, through and about the anode. Such pre-processing includes shaping an anode and providing surface and interior features (e.g., through-holes, ports, bores, tunnels, channels, irregular surface features and the like) to provide what are referred to herein as advanced valve metal (AVM) anodes. Pre-processing of AVM anodes prior to formation of oxide on the exterior and exposed interior surfaces of a pressed and sintered anode provides for robust, compact AVM capacitors for IMDs. The inventors recognized that forming valve metal anodes to high voltages, greater than about 200 V, frequently results in structural failure of the anode and that uniquely shaped anodes according to the present invention provide superior high voltage anode electrodes.

One significant aspect of the present invention includes enhanced circulation of liquid electrolyte—both formation electrolyte and working electrolyte. Due to enhanced electrolyte circulation (including electrolyte replenishment during formation) the active energy density of the capacitor may be increased (e.g., by altering anode porosity). The present invention offers advantages, particularly as compared with prior art capacitors and methods for fabricating, forming and operating capacitors in conjunction with IMDs such as ICDs as well as other medical devices that may frequently charge and therapeutically discharge one or more high voltage capacitors, as may be employed in clinics and hospitals. The AVM anodes of the present invention can be designed to optimize package efficiency of an IMD. According to the present invention perforated and non-perforated AVM anodes, with complex and irregular geometric shapes, may be efficiently provided that enhance the overall packaging efficiency of compact IMDs, such as ICDs. Such AVM anodes may be shaped to accommodate one or more elongated cathode members wherein the surface or interior features of the AVM anode correspond to the shape of the cathode member(s).

The inventors discovered that electrolyte circulation (or replenishment) is enhanced by, prior to formation, introducing an array of through-holes (e.g., channels, ports or apertures) into a pressed and sintered powder anode structure. The through-holes can have an arbitrary cross-sectional shape that optionally fluidly couple, or connect, opposing or adjacent exterior surfaces of the anode. Such through-holes in the anode are somewhat analogous to the human vasculature in which increasingly smaller diameter vessels are used for maximum circulation from a fluid source.

The inventors also discovered that for both sintered- and etched foil-type anodes, the porous electrode structure restricts movement of ions within the electrolyte necessary to complete the electrical circuit between anode and cathode. As a result, the equivalent series resistance (ESR) of the capacitor increases if the anode thickness is increased in an attempt to increase the active energy density of the capacitor. The introduction of an array of through-holes in the face or side surfaces of the anode slug (or etched foil stack) improves ESR (i.e., decreases ESR).

According to the present invention, the surface features and through-holes may be manually or automatically formed during or after pressing a raw AVM anode, or some may be introduced during pressing and some introduced subsequent to pressing the AVM anode to a desired shape or density. In addition, some or all such features and through-holes may be introduced after sintering a pressed anode. The features and/or through-holes can receive a variety of components or materials therein. For example, a material that absorbs liquid electrolyte, a cathode material, a relatively different density metallic powder, and the like.

The present invention takes advantage of the small size and shape flexibility of powdered metal anodes so that highly compact and ergonomic IMDs can be produced. In comparison to aluminum plate, flat electrolytic capacitors (FECs) having hundreds of discrete parts and components and require attendant complex manufacturing procedures, AVM anodes have few parts and relatively simple manufacturing procedures. Beginning with relatively pure powdered metal (often including a binder), a manufacturing process for AVM anodes according to the present invention involves pressing the powder to a given press-density and into a desired shape, washing the pressed anode, sintering the anode (at approximately 1300-1450 degrees Celsius in a reduced pressure atmosphere), washing the anode, annealing the anode (at 350 degrees Celsius in ambient air), and reforming the anode (to cure any oxide deformation from the annealing step).

A wide variety of perforated and porous AVM anodes according to certain embodiments of the present invention provide: (i) improved thermal characteristics (during anode formation), (ii) reduced ESR (especially important during operation of an AVM anode in an IMD), (iii) integrated, interlocking anode-cathode elements (high capacitance, insulated cathode rods inserted into at least some of said perforations), and (iv) increased and enhanced manufacturability due to ease of alignment of anode and cathode members during fabrication of capacitors built according to the present invention.

BRIEF DESCRIPTION OF THE DRAWINGS

These and other advantages and features of the present invention will be appreciated as the same becomes better understood by reference to the following detailed description of the various embodiments of the invention when considered in connection with the accompanying drawings, in which like numbered reference numbers designate like parts throughout. The drawings are not drawn to scale and are merely representative of just a few exemplary embodiments of the present invention. Other embodiments clearly within the scope of the present invention will be readily apparent to those of skill in the art, and each such embodiment is intended to be covered hereby, limited only by the claims appended hereto.

FIG. 1 is a perspective view of a pressed and sintered valve metal anode slug having an arbitrary shape and a series of through-holes formed in a major lateral surface of the anode slug and wherein a lead wire electrically couples to the anode slug.

FIG. 2 is a perspective view of a pressed and sintered valve metal anode slug having an arbitrary curved shape and a series of through-holes of varying shape formed in both a major lateral and a top surface of the anode slug and wherein a lead wire electrically couples to the anode slug.

FIG. 3 is an elevational view of a minor lateral surface of a pressed and sintered valve metal anode slug having a series of apertures formed therein.

FIG. 4 is a combined perspective view of a multi-layer, elongated high capacitance cathode structure that is adapted to be inserted into a through-hole of a fully formed valve metal anode.

FIG. 5 is a perspective view having some parts exploded that depicts three multi-layer, elongated high capacitance cathode structures aligned with three through-holes formed in a foil stack anode structure (and wherein optional separator material is not depicted).

FIG. 6a-d are perspective views of a capacitor housing, or can; an anode fabricated and formed according to one aspect of the present invention with a lead wire coupled thereto; a separator material; and a cathode, respectively.

FIG. 7 is a perspective view depicting an arbitrary curvilinear anode member fabricated and formed according to the present invention.

FIG. 8 is a cross sectional view with parts exploded of a few through-holes of an anode member fabricated and formed according to the present invention and with multi-layer cathode members depicted aligned with a corresponding through-hole.

FIG. 9 is a cross sectional view depicting alternative embodiments for through-holes of an anode member (and at least one blind hole) fabricated and formed according to the present invention.

FIG. 10 is an elevational view in cross section depicting an embodiment of the present invention wherein a pair of cathode members are disposed orthogonally with respect to a set of anode members and wherein some of said anode members are fabricated and formed according to the present invention.

FIG. 11 is an elevational view in cross section depicting an embodiment of the present invention wherein a pair of cathode members are disposed substantially parallel with respect to a stack of anode members and wherein some of said anode members are fabricated and formed according to the present invention and wherein at least one of said anode members is corrugated with respect to adjacent anodes.

FIG. 12 is an elevational view in cross section depicting a capacitor assembly comprising an anode member fabricated and formed according to the present invention disposed adjacent a cathode member which is mechanically and electrically coupled to a housing, or can, and wherein the can retains the capacitor assembly.

FIG. 13 is an elevational view in cross section of an anode assembly aligned but spaced from a cathode array and wherein the cathode array is coupled to a base portion which may comprise a housing, or can, for a capacitor assembly.

DETAILED DESCRIPTION OF THE ILLUSTRATED EMBODIMENTS

Figure 14:
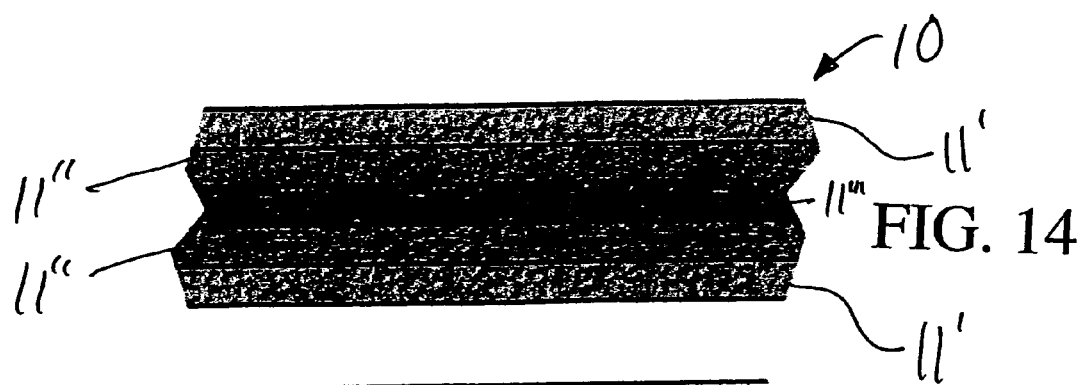
FIG. 14 is an elevational view in cross section depicting a part of a multi-layer anode member having a central layer of a high density, a first layer of an intermediate density adjacent to and substantially surrounding the central layer, and a second layer of a lowest density adjacent and substantially surrounding the first layer.

The present invention provides novel techniques, process and structure in fabricating and operating compact, high voltage, high capacitance and high energy density AVM anodes. As will be further detailed herein, various embodiments and forms of the present invention provide distinct advantages over the prior art. Also, even though only a few valve metals which are known for use in conjunction with IMDs are described in detail herein, the invention is not so limited. For example, any valve metal may be used when practicing the present invention as may other non-valve metal materials such as ceramic materials having a high dielectric constant (e.g., 12-400,000). By example and without limitation, the following materials may be used: tantalum, niobium, aluminum, zinc, magnesium, zirconium, titanium, hafnium, palladium, iridium, ruthenium, molybdenum including combinations and/or alloys thereof. Preferably, each of the foregoing should be susceptible of accurate, predictable control of oxide thickness during formation and the resulting oxides should be dense, tightly adhering and electrically insulative with high dielectric strength and a high dielectric constant. Finally, while the present invention is described primarily with respect to liquid electrolyte capacitors, solid electrolyte may be utilized in accordance with the present invention.

During anode pre-processing according to the present invention, the perforations, apertures and the like formed in the anode slug may have a geometric, conical, irregular and/or serpentine shape(s) and can be formed orthogonal to an local exterior surface region of the anode or at an angle to the surface region. The perforations, apertures and the like may intersect others below the surface of the anode; however, such apertures will likely only be suitable for receiving a single cathode member. In a desirable embodiment, a plurality of blind bores (i.e., apertures or bores that do not couple two surfaces of the anode) are formed in the anode slug.

The inventors performed experiments that revealed that tantalum AVM anodes having through-holes formed therein are fully formed to between about 220 V and 275 V in less than about 30 hours. The resulting thickness of the dielectric tantalum pent-oxide is approximately 450 nm. This compares very favorably the time required for formation of standard, pressed and sintered tantalum anodes—which typically take over about 100 hours before fully formed to a high voltage. The perforated AVM anodes designed, fabricated, formed and operated according to the present invention simply form metal oxides faster and more reliably than prior anode designs.

Experiments have shown a reduced ESR for capacitors fabricated according to the present invention. Typically the ESR of AVM anodes can be reduced by approximately fifty percent (50%) as compared to prior art capacitors. The inventors have discovered that the formation process for such anodes is typically two to three times (2×-3×) faster and the equivalent series resistance (ESR) is approximately half (50%) as compared to existing valve metal anodes. The present invention avoids difficulties encountered when applying high voltage (e.g., 200 volts) during anodizing of relatively thick (e.g., greater than 3 mm) AVM anodes. These difficulties include frequent failure of the material due, at least in part, to unequal thermal dissipation between interior open spaces of the sintered AVM anode and the formation electrolyte resulting in anode fractures.

The AVM anodes according to the present invention are particularly suited for use with a wet electrolyte although a variety of solid electrolyte materials may be successfully used. The AVM anodes preferably comprises a sintered member (i.e., a coherent mass of material produced by heating—but not melting—the material) formed of metallic powder. Tantalum, niobium or combined tantalum/niobium powders are preferred although other valve metal powders may be used. To fabricate anode members according to the present invention, a chosen metallic powder is pressed into a selected shape or configuration and then heated in a pressure vacuum to approximately 1500 degrees Celsius. Although in most embodiments of the present invention the pre-processing occurs subsequent to pressing but prior to sintering of a powdered valve metal anode slug, optionally, the anode slug may be perforated (i.e., pre-processed) after sintering but prior to anodization, as further described herein.

In either event, according to the present invention the sintered (and perforated) anode slug is immersed in a liquid electrolyte in the presence of a source of electrical potential (i.e., for anodization). While outside the scope of the teaching of the present invention, such anodization processing is required to form a sufficient depth of oxide on the anode surface.

As is known in the art, the magnitude of the electrical potential may vary although approximately two hundred volts are preferably used. As a result an oxidation film grows over all exposed surfaces of the perforated sintered slug. For the desired medical device applications (e.g., ICDs), this oxidation film must reach at least a thickness of approximately one-half (½) micron, which corresponds to approximately 200 volts, although 250 volts or greater magnitude potential may be applied.

The pre-processed anodes according to the present invention preferably utilize an improved method for anodizing as described in co-pending, non-provisional patent application Ser. No. 10/058,437 filed 28 Jan. 2002 by Joachim Hossick-Schott and entitled, "Methods of Anodizing Valve Metal Electrodes." The entire contents of which are hereby incorporated herein. In this application an inventive method is disclosed wherein the anode is anodized by: immersing the pressed valve metal anode in an anodizing electrolyte to wet the anode and develop an anode-electrolyte system and subjecting the anode-electrolyte system to a potential that is ramped up from a starting potential to a target potential in a pulsed fashion whereby both formation current and formation potential are delivered to the anode in a pulsed fashion. The applied pulses are preferably decreased in pulse width as the formation potential increases. The pulse width of the applied pulses is preferably defined as the duty cycle of the formation potential pulses. The duty cycle may decline from one hundred percent (100%) in the low formation potential regime to as low as one percent (1%) in the vicinity of the target formation potential. After reaching the target formation potential, the potential pulses with a pulse height equal to the target formation potential are preferably applied for a hold time until the amplitude of the current pulses becomes small.

With respect to the cathode for capacitors fabricated according to the present invention, the cathodes may be electrically insulated from the housing, or can, which surrounds the capacitor or it may be electrically and/or physically bonded to the can. In one embodiment, the cathode comprises at least one elongated member having a core, a high capacitance coating surrounding the core and a non-conductive coating surround the high capacitance coating. An aperture of the anode is thus configured to receive the elongated cathode member, resulting in a compact integrated capacitor. Electrically conductive lead wire may then be connected to the can or to a separate cathode feedthrough wire. That is, the cathode may be either electrically coupled to the can. One form of this embodiment involves an array of apertures (and/or blind bores) formed in the anode and a corresponding array of cathode members. In an embodiment having blind bores formed in the anode, the elongated cathode members preferably are coated with high capacitance material on all sides that lie adjacent anode material (i.e., the sides and end portion(s) inserted into the blind bore should all be coated). When coupled together a compact capacitive structure results with the added benefit of ease of assembly because the cathode array is readily aligned with the anode apertures. This form of the invention may be practiced with a single sintered anode slug or with two (or a plurality of) thin foils of valve metal material (each having a stable oxide formed thereon). Of course, when using thin foil a separator sheet (or other insulation materials) should be interposed between adjacent cathode and anode.

In another form of the present invention, at least two powdered valve metal materials each having a different density (and/or pressed to a different press-density) may be employed. In one variation to this form of the invention a fibrous material, a cellulose material, or other relatively resilient material that can be added to the powder composition prior to pressing the anode. Such material should be susceptible of withstanding compression during pressing of the anode, readily removable (e.g., dissolve in a fluid and/or fully incinerate during sintering), and effectively impregnated with liquid electrolyte. Such material can be advantageously disposed around the periphery portions of the raw anode prior to pressing and removed prior to formation to even further promote circulation of the formation and working electrolyte. Of course, such material may be substantially homogenously distributed throughout the anode structure while still providing advantages according to the present invention.

FIG. 1 is a perspective view of an anode assembly 10 having a pressed and sintered valve metal anode slug 11 having an arbitrary shape and a series of through-holes 12 formed in a major surface 17 of the anode slug 11 and wherein a lead wire 14 electrically couples the anode slug 11 to an external electrical circuit (not shown). As depicted the through-holes 12 appear to have a circular cross section and are somewhat randomly distributed across the major surface 17. However, the through-holes may possess any convenient geometric shape and may be uniform in cross section or may vary in cross section as will be appreciated by one of skill in the art to which the invention is directed.

The major surface 17 (and the opposing major surface—not depicted) of the anode slug 11 depicted in FIG. 1 has a substantially flat major surface 17 terminating on one side in a straight edge portion and a second side terminating in a uniformly curved peripheral edge. However, the particular shape of an anode slug 11 fabricated according to the present invention may be of any arbitrary shape to accommodate a particular desired shape and/or to minimize the volume of the anode slug 11 relative to other parts an integrated device such as an IMD.

FIG. 2 is a perspective view of an anode assembly 10 comprising a pressed and sintered valve metal anode slug 11 having an arbitrary curved shape and a series of through-holes 12 of varying shape formed in both a major lateral surface 17 and a minor top surface 19 of the anode slug 11 and wherein a lead wire 14 electrically couples to the anode slug 11. In FIG. 2, while the through-holes 12 have various geometric shapes and are randomly distributed around the anode slug 11 the through-holes 12 may have a uniform cross section and may be uniformly distributed relative to each other through-hole. Furthermore, the major surface 17 of the anode slug 11 is shown having a substantially uniform curved shape but the anode slug 11 may assume myriad other arbitrary shapes. The anode slug 11 may be pressed into virtually any arbitrary shape. For example, an opposing pair of cooperating mold parts having a reverse geometry shape formed therein may be used to compress the anode slug 11 into a desired shape. The mold parts may have convex, concave, irregular, curved or geometric features formed therein to impart a desired shape to the anode slug 11. One or both of the mold parts may have one or more elongated members such as a shank, peg, pin or the like to form one or more through-holes 12 into the anode slug 11. Variations of the foregoing are expressly deemed to be covered by the teaching of the present invention.

In the event that a substantially planar cathode member (not shown) is utilized, however, such arbitrary shapes preferably should have substantially parallel surfaces to maximize energy density of the resulting capacitor. As can be appreciated with reference to FIG. 4 and FIG. 5 certain embodiments of the present invention do not utilize planar cathode members and thus are not constrained with respect to the shape of such capacitors. That is, a series of elongated cathode assemblies of varying length having high capacitance material disposed thereon (and electrically insulated from the anode slug 11) may be used according to the present invention.

FIG. 3 is an elevational view of a minor lateral surface of a pressed and sintered valve metal anode slug 11 having a series of apertures 12 formed on a minor surface 19 thereof. The apertures 12 depicted in FIG. 3 are arranged in a linear array having substantially equivalent spacing therebetween.

FIG. 4 is a combined perspective view of a multi-layer, elongated high capacitance cathode assembly 20 that is adapted to be inserted into a through-hole 12 of a fully formed valve metal anode 11. The cathode assembly 20 comprises a core member 22 surrounded by a layer of high capacitance material 24 which in turn is covered with an electrical insulator separator material 18. While as depicted in FIG. 4, the cathode assembly 20 appears as a uniform shank, the cathode assembly (and core 22) may assume a variety of different shapes. The cathode assembly 20 is intended to be inserted into a through-hole 12 roughly corresponding in shape to the cathode assembly 20. The cathode assembly 20 may be fully or partially inserted into a given through hole 12 and an array of such cathode assemblies 20 may have a common configuration or diverse configurations. One desirable high capacitance material 24 is a layer of carbon (and/or a titanium carbide), or a ruthenium oxide film forming or covering the core 22 that, as depicted in FIG. 4, may comprise a titanium rod. In embodiments of the present invention that utilize such a cathode assembly 20, not every through-hole 12 is required to have a corresponding cathode assembly 20 inserted therein. In fact, while not depicted a combination of a conventional planar cathode assembly and a discrete set of cathode assemblies 20 may both be employed in a single capacitor.

While one or more cathode assemblies 20 are depicted in FIG. 4, one or more of the through-holes 12 may remain empty or may be filled with a material that absorbs (e.g., wicks) and/or retains liquid electrolyte (e.g., a non-woven material, a cellulose fiber, a paper and the like). In addition or in lieu of the foregoing, the through-holes 12 may be filled with a different grain size or dimension metallic powder. The metallic powder may be packed or compressed into a through-hole 12 prior to or after performing a sintering step, if desired.

FIG. 5 is a perspective view having some parts exploded that depicts three multi-layer, elongated high capacitance cathode structures 20 aligned with three through-holes 12 formed in a foil stack anode assembly 10 (and wherein optional separator material is not depicted). In addition, an elongated conductor 28 couples the cathode assemblies 20 together. In lieu of such an elongated conductor 28, the core 22 of the cathode assembly 20 may be electrically (and optionally, mechanically) coupled to an electrically conductive housing, or can (not shown). While only three cathode assemblies 20 are depicted in FIG. 5 for ease of reference, many more may be utilized in a given capacitor application. Since the cathode assemblies 20 are each individually insulated from the anode assembly 10, no separator layer 18 (or other dielectric material) is required for this particular embodiment of the invention. Also, although a single anode slug 11 may be used in lieu of the foil stack anode assembly 10 depicted in FIG. 5. Furthermore, and as will be described in further detail herein, if a foil stack assembly 10 is used, one or more of the individual foil plates 11 may be prepared according to the present invention to improve circulation of electrolyte therearound. A few techniques for improving such circulation include drilling, etching, die cutting and other techniques to render a more porous foil plate 11.

FIG. 6a-d are perspective views of a two piece electrically conductive capacitor housing, or can 30 (and opposing side 32—not depicted); an anode 11 having through-holes 12, which is fabricated and formed according to one aspect of the present invention with a lead wire 14 coupled thereto; a separator material 18; and a cathode 20, respectively. FIG. 6a-d depict a preferred configuration for a capacitor assembly suitable for use in conjunction with an IMD. The cathode assembly 20 in this embodiment is of conventional design; that is, a titanium foil having a thin oxide (such as ruthenium oxide) formed thereon. The cathode assembly may be electrically and/or mechanically bonded to the can 30 (or 32) and the separator 18 is interposed between the anode assembly 10 and the cathode assembly 20.

FIG. 7 is a perspective view depicting an arbitrary curvilinear anode member 11 fabricated and formed according to the present invention. In FIG. 7 the anode member 11 has a plurality of through-holes 12 formed through adjacent major surfaces 17. The elongated cathode assemblies 20 described and depicted with respect to FIG. 4 are suitable for use in conjunction with the anode 11 although the cathode assemblies 20 would preferably have a length dimension closely corresponding to the depth of the through-hole 12 into which the cathode assembly 20 is to be inserted.

FIG. 8 is a cross sectional view with parts exploded of a few through-holes 12 of an anode member 11 fabricated and formed according to the present invention and with multi-layer cathode members 20 depicted aligned with a corresponding through-hole 12.

FIG. 9 is a cross sectional view depicting alternative embodiments for through-holes 12 of an anode member 11 (and at least one blind hole 12) fabricated and formed according to the present invention.

FIG. 10 is an elevational view in cross section depicting an embodiment of the present invention wherein a pair of cathode assemblies 20 are disposed orthogonally with respect to a set of anode members 11 and wherein some of said anode members 11 are fabricated and formed according to the present invention.

FIG. 11 is an elevational view in cross section depicting an embodiment of the present invention wherein a pair of cathode assemblies 20 are disposed substantially parallel with respect to a stack of anode members comprising an anode assembly 10 and wherein some of said anode members 11 are fabricated and formed according to the present invention and wherein at least one of said anode members 11 is corrugated with respect to adjacent anodes 11. In FIG. 11 at least one of the cathode assemblies 20 is not particularly elongated but rather may be shaped substantially like a discrete cone or a ridge member.

FIG. 12 is an elevational view in cross section depicting a capacitor assembly comprising an anode member fabricated and formed according to the present invention disposed adjacent a cathode member which is mechanically and electrically coupled to a housing, or can, and wherein the can retains the capacitor assembly.

FIG. 13 is an elevational view in cross section of an anode assembly 10 aligned but spaced from a cathode array 20 and wherein the cathode array 20 is coupled to a base portion 30,32 which may comprise a housing, or can, for a capacitor assembly.

FIG. 14 is an elevational view in cross section depicting a part of a multi-layer anode member 10 having a central layer 11''' of a high density, a first layer 11'' of an intermediate density adjacent to and substantially surrounding the central layer 11''', and a second layer 11' of a lowest density adjacent and substantially surrounding the first layer 11''. While not depicted, the first and second layers 11'',11' may be of different thickness than the central layer 11'''. Also, preferably the first and second layers 11'',11' completely surround the central layer 11''' so that the mean transport path for electrons initially situated on a surface portion of the central layer 11' is substantially equal with respect to the nearest exterior surface location of the second layer 11'. The respective portions of the layers disposed on opposing sides of the central portion 11''' are preferably coupled together. Of course, more than three layers may be implemented in accordance with the present invention.

Figure 15:
FIG. 15 depicts a portion of an anode member having a gradual density gradient from a central portion to a peripheral portion and wherein the central portion has a highest density is and the peripheral portion has a lower density.
Figure 16:
FIG. 16 depicts a portion of an anode member having a less gradual density gradient than the portion depicted in FIG. 15 such that a major central portion has a highest density and a minor peripheral portion has a density lower than the central portion.

FIG. 15 depicts a portion of an anode member 10 having a gradual density gradient from a central portion 11''' to a peripheral portion 11' and wherein the central portion 11''' has a highest density and the peripheral portion 11' has a lower density. FIG. 16 depicts a portion of an anode member 10 having a less gradual density gradient than the portion depicted in FIG. 15 such that a major central portion 11''' has a highest density and a minor peripheral portion 11' has a density lower than the central portion 11'''. In the embodiments depicted in FIGS. 15 and 16, a substantially linear gradual density gradient is depicted and a less linear density gradient is depicted, respectively.

In the FIGS. 14-16, the varying density characteristics of the respective portions of the anode member 10 may be accomplished in a variety of ways. For example, granular material that is soluble in water or other aqueous solution may be added to the powdered valve metal prior to pressing. Then, the raw pressed anode member 10 may be flushed to remove the granular material. In a similar manner other materials may be used; such as, granular materials that are readily incinerated when heated or subjected to flame, materials that melt (particularly if little or no residue remains), and the like. As with other embodiments of the present invention, mechanical appliances may be used to perforate or bore through all or a portion of the anode members depicted. Such perforations or bores may penetrate the entire anode member 10 or may penetrate to the central layer 11'''. Those of skill in the art will surely recognize variations of the described and/or depicted techniques for selectively altering the density of portions of an valve metal anode member 10 and all such variations are intended to be covered hereby. For example, a density profile or gradient may result from differing dimension of grains of metallic material, differing binder included in the powdered metallic material, differing press-density imparted to the powdered metal and the like. In addition, the pressing sequence may comprise a single compression step to a single press-density, a two- to three-step compression step and/or an accelerated compression stroke to thereby impart different density to an anode slug.

The following examples are set forth as various examples of the present invention and are meant as illustrative and not limiting as to the scope and breadth of the present invention.

EXAMPLE 1

A method of fabricating a valve metal anode, comprising the steps of:
depositing a metallic powder in a receiving container;
applying pressure to the metallic powder to form a raw anode at a first press-density;
removing the raw anode from the container;
removing portions of the raw anode;
sintering the raw anode;
depositing the raw anode in an electrolyte solution; and
applying electrical potential to the raw anode until an oxidation layer forms to a desired thickness on exposed portions of the raw anode.

EXAMPLE 2

A method according to example 1, wherein the depositing step b) further comprises:
b1) depositing a first layer of the metallic powder having a first density characteristic;
b2) depositing a second layer of the metallic powder having a second density characteristic which is different from said first density characteristic, on top of said first layer of metallic powder.

EXAMPLE 3

A capacitor apparatus, comprising:
a porous sintered valve metal anode member having at least two cavities formed therein and having a layer of oxide formed on exposed surfaces of the anode member and wherein said valve metal anode has a cross-sectional density profile wherein a peripheral portion of the valve metal anode is less dense than a central portion of the valve metal anode;
a conductive lead wire coupled to the anode member;
at least one cathode member disposed in electrical communication with said anode member; and
a housing means for retaining the anode member and cathode member.

EXAMPLE 4

A high energy-density valve metal anode, comprising:
a multi-density, layered porous sintered valve metal anode member having a layer of oxide formed on exposed surfaces of the anode member and wherein said valve metal anode has a cross-sectional density profile wherein an outmost layer that is less dense than the density of a central layer of the valve metal anode; and
a conductive lead wire coupled to the anode member.

EXAMPLE 5

An anode member for a high energy density capacitor apparatus, comprising:
a porous sintered valve metal anode member assembly having a central layer, a first layer substantially surrounding said central layer, and a second layer substantially surrounding said first layer, wherein the central layer comprises a high density member, the first layer comprises a lower density member, and said second layer comprises a lowest density member and wherein said central, said first, and said second layer are independently pressed and sintered, and then combined and anodized together in a formation electrolyte solution so that a layer of oxide is formed on exposed surfaces of each of said central, said first, and said second layers; and
a conductive lead wire coupled to a portion of said anode member.

EXAMPLE 6

An anode member according to example 5, wherein said central layer, said first layer and said second layer have a plurality of apertures formed therein adapted for receiving a like plurality of elongated cathode members arranged in an array and wherein the interior of said plurality of apertures are covered with an electrically non-conductive material so that when said elongated cathode members are inserted therein said anode member and said plurality of elongated cathode members are not in direct electrical communication.

The relevant portion(s) of all patents and printed publications disclosed herein are hereby incorporated by reference herein into the specification hereof.

The preceding specific embodiments are illustrative of an anode formation process for anodes usable in capacitors, particularly capacitors incorporated into an IMD, in accordance with the present invention. It is to be understood, therefore, that other expedients known to those skilled in the art or disclosed herein, and existing prior to the filing date of this application or coming into existence at a later time may be employed without departing from the invention or the scope of the appended claims.

The invention claimed is:

1. A capacitor apparatus, comprising:
   a porous sintered valve metal anode member having at least two cavities formed therein;
   a conductive lead wire coupled to the anode member;
   at least one cathode member disposed in electrical communication with said anode member; and
   a housing means for retaining the anode member and cathode member,
   wherein said valve metal anode includes a cross-sectional density gradient and a peripheral portion of the valve metal anode is relatively less dense than a central portion of the valve metal anode.

2. A capacitor apparatus according to claim 1, wherein the central portion comprises a substantially uniform shape.

3. A capacitor apparatus according to claim 1, wherein the peripheral portion includes at least one elongated hollow passageway.

4. A capacitor apparatus according to claim 3, wherein the at least one elongated hollow passageway is occupied by a material.

5. A capacitor apparatus according to claim 4, wherein the material is one of: a material that absorbs liquid electrolyte, a cellulose-based material, a cathode material, a non-woven material, a metallic powder of different density than the density of the peripheral portion.

6. A capacitor apparatus according to claim 5, wherein the metallic powder has a different density than the density of the central portion.

7. A capacitor apparatus comprising:
   a porous sintered valve metal anode member having at least two cavities formed therein;
   a conductive lead wire coupled to the anode member;
   at least one cathode member disposed in electrical communication with said anode member; and
   a housing means for retaining the anode member and cathode member,
   wherein the cathode member includes one of: a carbon material, stainless steel material, a carbide material, a titanium material and a ruthenium material;
   wherein said cathode member comprises an elongated cathode member and said elongated cathode member is at least partially inserted into one of said at least two cavities, and wherein said cathode member has a core surrounded by a high capacitance material and a separator layer surrounding the high capacitance material.

8. An apparatus according to claim 7, wherein the anode member includes one of: an aluminum material, a tantalum material, a niobium material, a valve metal material, and an alloy comprising at least one valve metal.

9. An apparatus according to claim 7, wherein the at least two cavities comprises at least one surface feature on the anode member and said at least one surface feature comprises one of: a ridge, a boss, a channel, a tunnel, a corrugation, a ripple, a groove, a notch, a slot, a furrow, and a crease.

10. An apparatus according to claim 7, wherein said cathode member includes a coat of at least one of: a carbon layer, a carbide material, a carbonaceous material, a ruthenium oxide, an iron oxide, a nickel oxide, a titanium oxide, a ruthenium carbide, an iron carbide, and a nickel carbide.

11. A capacitor apparatus, comprising:
    a porous sintered valve metal anode member having at least two cavities formed therein;
    a conductive lead wire coupled to the anode member;
    at least one cathode member disposed in electrical communication with said anode member; and
    a housing means for retaining the anode member and cathode member,
    wherein said cathode member comprises an elongated cathode member and said elongated cathode member is at least partially inserted into one of said at least two cavities, and wherein said cathode member has a core surrounded by a high capacitance material and a separator layer surrounding the high capacitance material.

12. An apparatus according to claim 11, wherein the at least one elongated cathode member further comprises a coaxial, nested set of hollow core members, and wherein said core members have a layer of one of the following disposed thereon: a carbon, a carbide, a metal oxide.

13. A capacitor apparatus, comprising:
    a porous sintered valve metal anode member having at least two cavities formed therein;
    a conductive lead wire coupled to the anode member;
    at least one cathode member disposed in electrical communication with said anode member; and
    a housing means for retaining the anode member and cathode member,
    wherein said anode member and said cathode member each have major surfaces and the major surface of the anode member is disposed substantially orthogonal to the major surface of the cathode member.

14. An apparatus according to claim 13, further comprising:
    a pair of cathode members disposed spaced apart so that the major surfaces of the pair of cathode members are substantially parallel; and
    a plurality of anode members disposed between the pair of cathode members and electrically insulated from each adjacent one of said plurality of anode members.

15. An apparatus according to claim 13, wherein at least one of said plurality of anode members has a plurality of apertures formed therein.

16. An apparatus according to claim 15, further comprising at least one layer of porous material disposed between an adjacent pair of anode members.

17. An apparatus according to claim 16, wherein said at least one layer of porous material is an aluminum foil having a lower capacitance value than the anode members.

18. An apparatus according to claim 17, wherein the aluminum foil is mechanically etched with tunnel features oriented substantially parallel to the major surface or substantially orthogonal to the major surface.

19. An apparatus according to claim 18, wherein the aluminum foil is a relatively thick foil.

* * * * *